United States Patent [19]

McKoy et al.

[11] Patent Number: 4,622,174

[45] Date of Patent: Nov. 11, 1986

[54] TRANSPARENT PROTECTIVE LASER SHIELD

[75] Inventors: Vincent McKoy, Flintridge; Amitave Gupta, Pasadena, both of Calif.

[73] Assignee: Barnes Engineering Company, Stamford, Conn.

[21] Appl. No.: 617,320

[22] Filed: Jun. 5, 1984

[51] Int. Cl.[4] ............................ G02B 5/28; G02F 1/01; H01S 3/10; H03F 7/00

[52] U.S. Cl. .................................... 252/582; 350/311; 350/353; 372/21; 307/425

[58] Field of Search ................ 252/582, 600; 350/311, 350/353; 260/429 R, 429 CY, 429 J; 307/425; 372/21

[56] References Cited

U.S. PATENT DOCUMENTS

| 2,155,038 | 4/1939 | Davies ................................. 260/314 |
| 2,861,005 | 11/1958 | Siegel ................................. 106/288 |
| 3,091,618 | 5/1963 | Fleysher ........................... 260/314.5 |
| 3,148,933 | 9/1964 | Randall ................................. 8/1 |
| 3,291,746 | 12/1966 | Donoian ............................. 252/300 |
| 3,687,863 | 8/1972 | Wacher .............................. 252/582 |
| 3,696,263 | 10/1972 | Wacher ........................... 252/582 X |
| 3,743,964 | 7/1973 | Drexhage ....................... 252/582 X |
| 3,853,783 | 12/1974 | Tucker .............................. 252/300 |
| 3,900,323 | 8/1975 | MacLeish ...................... 252/582 X |

FOREIGN PATENT DOCUMENTS 60-43605  3/1985  Japan ................................... 252/587

OTHER PUBLICATIONS

Yardley, et al., "Laser-Produced Ultrafine Powders and Appl.", Reza Kenkyu, 12(7) 394–400, 1984.
Huang, et al., "Electronic Transitions of Vanadyl Phthalocyanine", Chemical Physics, 65 (1982) 205–216.
Kivits, et al., "Vanadyl Phthalocyanine . . . ", Appl. Phys., A26, 101–105 (1981).
Pyatosin, "Study of the Photophysics", Opt. Spectrosc., (USSR) 52(2) Feb. 1982, 162–166.
Varnavskii, et al., "Self-Synchronization of Laser", Sov. Tech. Phys. Lett., vol. 2, No. 10, Oct. 1976.
Byteva, et al., "Quenching of Sensitized Luminescence", Russ. J. Phys. Chem., 56(7) 1982, pp. 1056–1058.
Morinaka, et al., "Optical Recording Media . . . ", Appl. Phys. Lett., 43(6), 15, Sep. 1983, pp. 524–526.
Shirai, et al., "Functional Metal-Porphyrazine . . . ", Makromol. Chem., 180, 2073–2084 (1979).

Primary Examiner—John F. Terapane
Assistant Examiner—Catherine S. Kilby
Attorney, Agent, or Firm—Parmelee, Bollinger & Bramblett

[57] ABSTRACT

A transparent protective laser shield and a method for forming the same are provided in which the shield is adapted to be interposed between a laser beam and a viewer for adjustably absorbing more than one narrow band radiation from laser beams while transmitting radiation in a broader band surrounding the narrow band laser beams. A transparent host material comprising a crystalline or amorphous glassy or plastic material having substantial transmission properties of optical radiation has introduced therein a plurality of chromophores selected from a porphyrin complex which has been modified by a metal providing metallo-porphyrin complexes in the transparent material which absorbs optical radiation at predetermined narrow band wave lengths located within the selected broad band wave length passed by the transparent host material. The predetermined narrow band wave lengths absorbed in the transparent material is adjusted to match the desired laser wave lengths by adding radical groups to the metallo-porphyrin complexes to match the absorption bands in the transparent material forming the transparent protective laser shield to desired laser wave lengths. The viewer is enabled to see through the transparent laser shield but is protected from the laser beams which are absorbed by the shield to protect the viewer.

2 Claims, 3 Drawing Figures

TRANSPARENT PROTECTIVE LASER SHIELD

BACKGROUND OF THE INVENTION

This invention relates to a transparent protective laser shield which is adapted to be interposed between the laser beam and a viewer for protecting the viewer from damage by laser beam radiation, and more particularly, to such a shield against multiple wave lengths in which the absorption wave lengths are adjustably matched to that of laser beams of the type which the viewer is to be protected against.

In many medical, industrial, and other applications, the laser beam is employed for cutting, fusing, and other functions which may cause contact with the eye either by direct viewing or reflection from the object being worked on. Since the eye collects and focuses the energy, and since the laser beam is generally concentrated, considerable damage can result from the application of this energy to the optic nerve. The same is true in industrial applications when the viewer happens to be a light sensitive detector which may be monitoring the particular operation being performed by the laser. In such applications the laser energy which may use different lasers having different wave lengths may not be the wave lengths of interest, and therefore the application of the concentrated laser beams onto the detector may in fact destroy the detector and prevent the monitoring of the particular operation in other wave lengths. Accordingly, in this and other applications, it would be very advantageous to be able to view the laser beam and its environment without being subjected to the danger of the concentrated laser beam energy. In so viewing the laser beam through a suitable protective window, shield, or visor, it will also be extremely advantageous to be able to adjust the various wave lengths absorbed within certain narrow limits so that the construction of the particular protective shield may be varied slightly to exactly conform in its absorption characteristics with that of multiple laser beams to which the viewer is subjected and wishes to be protected against. The elimination of these very narrow and specific wave lengths will not generally detract from or make the passed broad band of optical radiation unintelligible.

SUMMARY OF THE INVENTION

Accordingly, it is an object of this invention to provide a transparent optical protective laser shield which absorbs optical radiation in selected narrow band widths and transmits a broad band of optical radiation which includes and/or surrounds the absorbed narrow band wave lengths which match the laser beam desired to be protected against.

Another object of this invention is to provide a transparent optical laser shield which has substantial transmission of optical radiation within a broad wave length band of interest.

Still a further object of this invention is to provide a transparent optical laser shield which absorbs narrow band wave lengths which can be adjusted to coincide with selected wave lengths of the laser beams which are desired to be protected against.

In carrying out this invention in one illustrative embodiment thereof a transparent protective laser shield and a method for forming the same are provided which shield is adapted to be interposed between a laser beam and a viewer for adjustably absorbing the narrow band laser beam radiation in more than one band while transmitting optical radiation in a broader band which includes the narrow band laser beams. The protective shield is formed by selecting a transparent host material having substantial transmission properties of optical radiation of a selected broad band and introducing into the host material chromophores selected from a porphyrin complex which has been modified by metals thereby providing metallo-porphyrin complexes in the transparent material which absorb optical radiation at predetermined narrow band widths located within the selected broad band wave length which is passed by the host material. The predetermined narrow band wave lengths absorbed in the transparent material are adjusted to match desired laser wave lengths by the addition of radical groups to the metallo-porphyrin complex thereby matching the absorption band of the transparent material to the desired laser wave length for protecting the viewer from the laser beam by the absorption of a substantial portion of the laser beam before it reaches the viewer while still permitting the viewer to view the laser beam and its environment.

U.S. Pat. No. 3,853,783 describes the use of vanadyl phthalocyanine sulfonamides in plastic compositions to protect the eyes from exposure to laser radiation with wave lengths in the region of about 620 to 720 nanometers. The invention is limited to one compound for a band which is not indicated to be adjustable or capable of being narrow. In addition, the protection does not extend to the other important wave lengths for lasers in common use e.g. the double YAG laser at 532 nm, or would protection be afforded for say a combination of lasers at 532 and 694 nanometers.

BRIEF DESCRIPTION OF THE DRAWINGS

The invention together with further aspects, objects, features and advantages thereof will be more clearly understood from the following description considered with the following drawings.

DESCRIPTION OF THE PREFERRED EMBODIMENTS

In the description of the present invention, it should be pointed out that the viewer may be either the human eye of an individual or any various forms of radiation sensitive detectors such as a photo-multiplier tube, photodetector, camera tube, etc. which views a scene and is desired to be protected from a narrow band laser beam which is focused or otherwise gathered or collected by an optical system and applied to the detector or human eye.

The present method and transparent protective laser shield, window, visor or goggles is adapted to prevent injury to the viewer by dissolving chromophores in the transparent material which strongly absorbs a very narrow spectral band around the laser wave lengths to be protected against while at the same time having good transmission properties in a much broader band so that the viewer may still observe a field of view which contains the laser or laser beams. The chromophores are generally a functional group of chemical compounds that give rise to a color in a molecule and with the assistance of an auxochrome such as a hyperoxyl or amino groups produces a dye. In the past such dyes have been used for coloring in textiles and for the same purpose when introduced into crystals, glasses, plastics or polycrystalline materials. The aforesaid patent used one specific compound in a transparent material to absorb specific rather broad wave lengths namely, 620–720 nm, in broader spectral bands where substantial transmission is available. In the present application different as well as a combination of chromophores in transparent material are provided for protection against laser injury in different as well as a combination of different wave lengths which will match and absorb the laser wave lengths. In accordance with this invention an adjustment or tuning of the absorption wave lengths of the chromophore is desirable and is provided.

Figure 1:
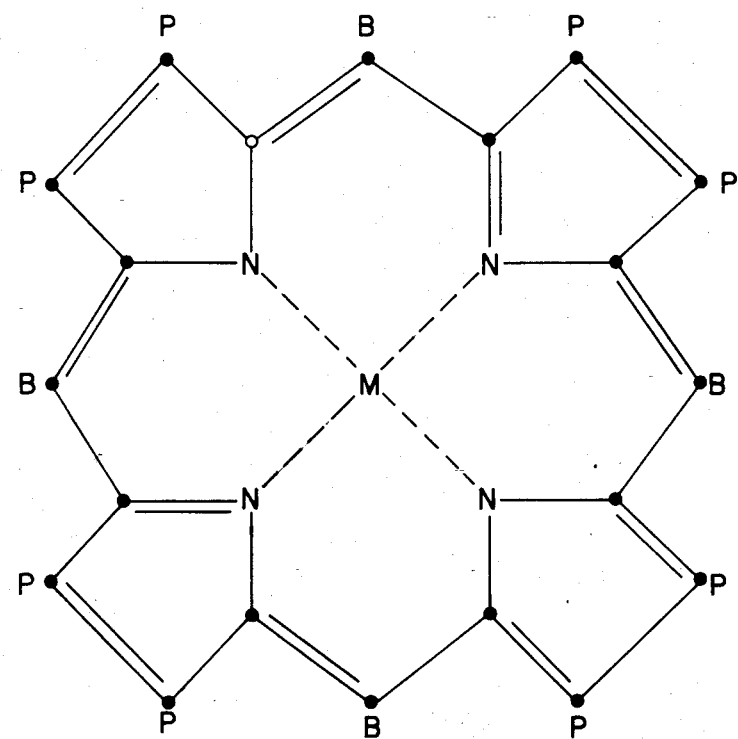
FIG. 1 illustrates the basic metallo-porphyrin molecule used in the present invention.

Metallo-porphyrin complexes have been found to be well suited for minor adjusting and tuning of an absorption wave length of a chromophore. The basic metallo-porphyrin molecule is illustrated in FIG. 1. It is characterized by a strong absorption band in the visible spectral region whose wave length depends upon a metal atom or metal oxide M located at the center of the molecule between four nitrogen atoms N. Many metals can be accepted by the porphyrin molecule thus providing a wide range of absorption band selection. However, the metal per se is not a sufficiently fine means of matching the absorption band to a given laser wave length. Accordingly, the addition of radical groups to the porphyrin molecule may be used to slightly shift the wave length of the absorption band established by the metal, and accordingly closely match the wave length of a laser beam which is desired to be protected against.

Returning to the basic metallo-porphyrin molecule shown in FIG. 1, four pentagonal rings called the pyrroles and radical groups can be substituted for the exo-pyrrole hydrogen atoms P and further substitutions can be made at the bridging groups B.

In accordance with the present invention, selecting a suitable metal or metals plus radical groups provides sufficient selectivity to place the absorption band at any desired location or locations within the spectral band. The chromophores so provided are introduced into crystal, glass, plastics or polycrystalline material or suspended in liquid form between two transparent glass or plastic plates to form the laser shield which may be in the form of a window, visor, shield or incorporated into goggles or otherwise interposed between the laser beam and the viewer in order to protect the viewer from the laser beam energy. The protective shield thus operates as a tunable or adjustable filter which absorbs the narrow bands in a much broader spectral band which is passed with transmission properties of at least 50%.

Figure 2:
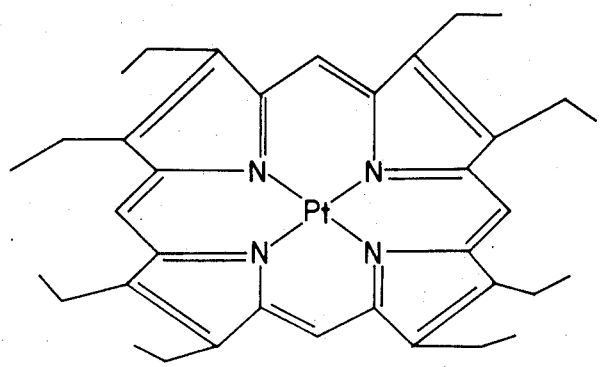
FIG. 2 illustrates the addition of platinum to the porphyrin complex of FIG. 1 modified by the addition of eight ethyl groups to produce platinum octaethylporphyrin which is used in the present invention to absorb the double YAG laser.

FIG. 2 illustrates an example of a modified metallo-porphryin complex which is suitable for use in a host material for absorbing the double YAG laser at 532 nanometers. In this example, the metal platinum is added to the porphyrin illustrated in FIG. 1 which can be made to absorb at 532 nanometers matching the narrow band wave length of the YAG laser by the addition of eight ethyl groups. The platinum complex of octaethylporphyrin is highly soluble in organic solvents so formed and concentrated methylmethacrylate films may be readily prepared.

Figure 3:
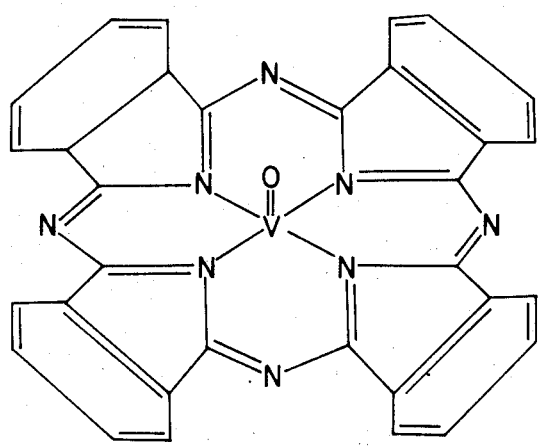
FIG. 3 illustrates the addition of the metal vanadium combined with the porphyrin of FIG. 1 to which are added the radical groups of four benzene rings and nitrogen atoms modifying the porphyrin to vanadyl phthalocyanine which is used in the present invention in combination with FIG. 2 in the same host material to absorb a ruby laser wave length in addition to the double YAG laser provided in FIG. 2.

The protection afford by the platinum complex described in connection with FIG. 2 in accordance with the present invention is combined with another metal complex to provide protection in two widely separated laser band widths. As an example, protection against a ruby laser wave length of 694 nanometers in addition to the double YAG laser at 532 nm may be made by adding vanadium-oxide which when combined with the porphyrin molecule causes the absorption band to be fairly close to the ruby laser wave length. This wave length can be shifted to coincide with the 694 nanometers by adding four benzene rings on the pyrrole bands and nitrogen atoms at the bridging points B to produce the modified porphyrin known as phthalocyanine resulting in the compound vanadyl phthalocyanine as illustrated in FIG. 3. This compound has an extremely sharp and intense absorption maximum at 694 nanometers, and accordingly is suitable for incorporation in a host material such as silica glass, or for example, methylmethacrylate. Combining octaethylporphyrin with vanadyl phthalocyanine in the host material will thus afford protection at both 532 and 694 nanometers.

In order to be effective the chromphores made up of the modified metallo-porphyrin complexes must be combined with the host materials of glass or plastic to produce optical densities in the range of 3 up to 12. Several methods may be employed which include dissolving the phthalocyanine derivatives and octaethylporphyrin which have been finely ground in the ball mill in a solvent which is mixed with the host material and heated to drive off the solvent. Another method includes finely grinding the modified metal porphyrins and mixing these with a fine powder of polymer for example, 125 mesh or finer which is thoroughly mixed to insure the proper dispersion of the chromophore prior to molding. The pre-mixtures are then compress molded at temperatures in excess of 150° C. for periods of up to two hours. The compression molding takes place in excess of 25,000 psi's with the samples being quenched in cold water before releasing the pressure.

By using these or similar methods solid shields or plates can be formed which are used as the transparent protective shields. The modified metallo-porphyrin derivatives may also be suspended in solution form between two transparent plates which may be interposed between the laser beam and the viewer for protecting the viewer. As previously pointed out, the viewer may be in the form of image tubes, vidicons, image intensifiers or other forms of radiation detectors as well as the human eye.

Thus, in accordance with the present invention, metallo-porphyrin complexes are provided using different metals which are readily accepted by the porphyrin molecule to provide a wide range of absorption band selection. Radicals are added to the porphyrin complexes to slightly shift the wave length of the absorption band established by the metal in the metallo-porphyrin complex to exactly match that of the wave length of a laser which is desired to be protected against. The chemical compounds forming the modified metallo-porphyrin complexes are incorporated into a host material which is transparent through a broad visual band such that the shield formed of the combined compound and host material may be formed into a window, goggles, shield, visor etc. which will pass a large portion of the visible radiation while absorbing the specific narrow band wave lengths of interest. Thus, the viewer whether it be a technical instrument, or the human eye can still view the field of view of the laser beam without the danger of being injured or destroyed.

Since other changes and modifications varied to fit particular operating requirements and environments will be apparent to those skilled in the art, the invention is not considered limited to the examples chosen for purposes of illustration, and includes all changes and modifications which do not constitute a departure from the true spirit and scope of this invention as claimed in the following claims and equivalents thereto.

What is claimed is:

1. A transparent protective laser shield which is interposed between a laser beam and a viewer for absorbing the narrow band laser beam radiation while transmitting optical radiation within a broader wave length band which includes the narrow band laser beam radiation comprising:

a transparent material having substantial transmission of optical radiation over a selected broad wave length band, said transparent material containing a chromophore of a porphyrin complex combined with platinum further modified by the addition of eight ethyl groups to said porphyrin complex thereby providing a chromophore of platinum octaethylporphyrin for establishing a strong absorption narrow wave length band for absorbing a double YAG laser beam radiation at approximately 532 nanometers, and said transparent material having said chromphore dispersed therein forming a laser shield having an optical density in the range of 3 to 12 which is interposed between the viewer and a laser beam for absorbing said double YAG laser beam while passing at least 50° of the optical radiation in said broad wave length band surrounding said narrow-band laser beam thereby protecting the viewer from said laser beam.

2. The protective laser shield set forth in claim 1 wherein said transparent material includes at least one additional chromophore dispersed therein of a porphryin complex combined with vanadium modified by benzene rings resulting in the compound vanadyl phthalcyanine for absorbing laser radiation from a ruby laser having a wave length of 694 nanometers whereby said laser shield protects from laser energy in at least two distinct and widely separated narrow band widths.

* * * * *

REEXAMINATION CERTIFICATE (1067th)
United States Patent [19]
McKoy et al.

[11] B1 4,622,174
[45] Certificate Issued May 30, 1989

[54] TRANSPARENT PROTECTIVE LASER SHIELD

[75] Inventors: Vincent McKoy, Flintridge; Amitave Gupta, Pasadena, both of Calif.

[73] Assignee: Barnes Engineering Company, Stamford, Conn.

Reexamination Request:
No. 90/001,551, Jul. 11, 1988

Reexamination Certificate for:
Patent No.: 4,622,174
Issued: Nov. 11, 1986
Appl. No.: 617,320
Filed: Jun. 5, 1984

[51] Int. Cl.$^4$ .......................... G02B 5/28; G02F 1/01; H01S 3/10; H03F 7/00
[52] U.S. Cl. .................................. 252/582; 350/311; 350/353; 372/21; 307/425
[58] Field of Search ................ 252/582, 600; 350/311, 350/353; 260/429 R, 429 CY, 429 J; 307/425; 372/21

[56] References Cited
PUBLICATIONS

Grigg et al, "Electrophilic Substitution Reactions of Metalloporphins," *Chemical Communications*, 1970, 1237–38.
Buchler et al, "Metallkomplexe mit Tetrapyrrol–Liganden, X", *Liebigs Ann. Chem.*, 1974, 1046–62.
Buchler, "Synthesis and Properties of Metalloporphyrins", in Dolphin (ed.), *The Porphyrins*, vol. I, pp. 389–483 (1978).
*Kirk–Othmer Encyclopedia of Chemical Technology*, vol. 2, pp. 659–663 (3d ed. 1978).
*McGraw–Hill Dictionary of Scientific and Technical Terms*, p. 1044 (1974).
Griffiths et al, "Polymorphism in Vanadyl Phthalocyanine," *Mol. Cryst. Liq. Cryst.*, 33, 149, 156–57 (1970).
Sherr et al, "Plastic Materials for Eye Protection from Lasers" (1972).
Sherr et al, "Adhesive Films for Laser Eye Protection" (1973).

*Primary Examiner*—John F. Terapane
*Assistant Examiner*—Catherine S. Kilby

[57] ABSTRACT

A transparent protective laser shield and a method for forming the same are provided in which the shield is adapted to be interposed between a laser beam and a viewer for adjustably absorbing more than one narrow band radiation from laser beams while transmitting radiation in a broader band surrounding the narrow band laser beams. A transparent host material comprising a crystalline or amorphous glassy or plastic material having substantial transmission properties of optical radiation has introduced therein a plurality of chromophores selected from a porphyrin complex which has been modified by a metal providing metallo-porphyrin complexes in the transparent material which absorbs optical radiation at predetermined narrow band wave lengths located within the selected broad band wave length passed by the transparent host material. The predetermined narrow band wave lengths absorbed in the transparent material is adjusted to match the desired laser wave lengths by adding radical groups to the metallo-porphyrin complexes to match the absorption bands in the transparent material forming the transparent protective laser shield to desired laser wave lengths. The viewer is enabled to see through the transparent laser shield but is protected from the laser beams which are absorbed by the shield to protect the viewer.

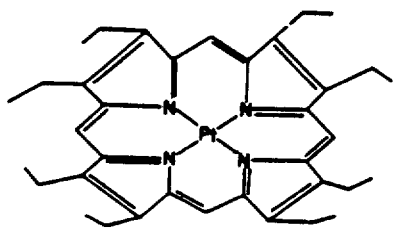

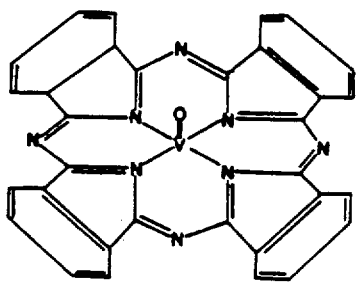

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 2 are cancelled.

* * * * *